United States Patent
Shah et al.

(10) Patent No.: US 9,918,911 B2
(45) Date of Patent: *Mar. 20, 2018

(54) META-STABLE COSMETIC OR SKIN CARE COMPOSITION

(71) Applicant: L'OREAL, Paris (FR)

(72) Inventors: Anil Shah, East Windsor, NJ (US); Jean-Thierry Simonnet, Mamaroneck, NY (US); Carlos Crissien, Clifton, NJ (US); Susan Halpern, Basking Ridge, NJ (US); Kevin Nikitczuk, Skillman, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/655,216

(22) PCT Filed: Dec. 24, 2013

(86) PCT No.: PCT/US2013/077642
§ 371 (c)(1),
(2) Date: Jun. 24, 2015

(87) PCT Pub. No.: WO2014/105878
PCT Pub. Date: Jul. 3, 2014

(65) Prior Publication Data
US 2015/0352016 A1   Dec. 10, 2015

Related U.S. Application Data

(60) Provisional application No. 61/746,194, filed on Dec. 27, 2012.

(51) Int. Cl.
| | |
|---|---|
| A61K 8/06 | (2006.01) |
| A61K 8/37 | (2006.01) |
| A61K 8/60 | (2006.01) |
| A61Q 19/00 | (2006.01) |
| A61K 8/49 | (2006.01) |

(52) U.S. Cl.
CPC ............... *A61K 8/062* (2013.01); *A61K 8/37* (2013.01); *A61K 8/375* (2013.01); *A61K 8/4993* (2013.01); *A61K 8/602* (2013.01); *A61Q 19/00* (2013.01); *A61K 2800/59* (2013.01)

(58) Field of Classification Search
CPC ........ A61K 8/062; A61K 8/375; A61K 8/602; A61K 8/4993; A61Q 19/00
See application file for complete search history.

(56) References Cited

U.S. PATENT DOCUMENTS 5,925,364 A * 7/1999 Ribier .................. A61K 8/0295
424/401
2009/0155371 A1 6/2009 Sojka et al.

FOREIGN PATENT DOCUMENTS

WO   WO 2008043470   *   4/2008

OTHER PUBLICATIONS

U.S. Appl. No. 13/727,739, filed Dec. 27, 2012, US 2014-018641, Anil Shah.
PCT/US13/77642, Dec. 24, 2013, WO 2014/105878, Anil Shah.
PCT/US13/77640, Dec. 24, 2013, WO 2014/105877, Anil Shah.

* cited by examiner

*Primary Examiner* — Mina Haghighatian
(74) *Attorney, Agent, or Firm* — McNees Wallace & Nurick LLC (57) ABSTRACT

A meta-stable composition, a product including the meta-stable composition, and a method of protecting a keratinous substrate from UV radiation by applying the product are provided. The meta-stable cosmetic composition includes at least one water-in-oil emulsifier having a hydrophilic-lipophilic balance (HLB) of less than 6, at least one non-ionic oil-in-water emulsifier having an HLB of greater than 9, at least one ionic surfactant, and at least one skin care active ingredient. The weight ratio of the at least one non-ionic oil-in-water emulsifier to the at least one water-in-oil emulsifier is about 0.02 to about 2.0. The meta-stable cosmetic composition converts from an oil-in-water (O/W) emulsion to a water-in-oil (W/O) emulsion upon rubbing.

21 Claims, 2 Drawing Sheets

META-STABLE COSMETIC OR SKIN CARE COMPOSITION

CROSS-REFERENCE TO RELATED APPLICATIONS

This patent application claims benefit of PCT Application Serial No. PCT/US2013/077642, filed on Dec. 24, 2013, entitled "META-STABLE COSMETIC OR SKIN CARE COMPOSITION"; which claims priority from U.S. Provisional Application Ser. No. 61/746,194, filed Dec. 27, 2012, entitled "META-STABLE COSMETIC OR SKIN CARE COMPOSITION," the disclosure of which are incorporated by reference as if fully rewritten herein.

FIELD OF THE INVENTION

The present invention is directed to a meta-stable cosmetic composition, products, and method of using the meta-stable cosmetic composition. More specifically, the present invention is directed to a meta-stable cosmetic composition that converts from an oil-in-water (O/W) emulsion to a water-in-oil (W/O) emulsion upon rubbing.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase. O/W emulsions are the ones most sought in the cosmetics field, since O/W emulsions comprise an aqueous phase as external phase, which gives them, when applied to the skin, a fresher, less greasy and lighter feel than W/O emulsions.

As water-in-oil (W/O) emulsion systems are close to the skin's hydrolipid film, they are more effective from the dermatological viewpoint. This emulsion type promotes the long lasting moisturizing efficacy by providing an occlusive film and reinforces the active ingredients into the stratum corneum. In addition, W/O emulsions leave a lipophilic film on the skin surface which ensures high water repellency, which is an important parameter to maintain high UV protection in sun care applications. Nevertheless, tackiness, combined with greasiness and slow spreading are key factors which tend to decrease cosmetic acceptance, thus counteracting W/O emulsion benefits.

Therefore, it is desirable to provide a meta-stable cosmetic composition that is applied as an oil-in-water (O/W) emulsion which quickly inverts to a water-in-oil emulsion (W/O) upon rubbing into the skin and that is pleasing to consumers.

A meta-stable cosmetic composition, product, and method of using the meta-stable cosmetic composition that do not suffer from one or more of the above drawbacks would be desirable in the art.

BRIEF DESCRIPTION OF THE INVENTION

In an exemplary embodiment, a meta-stable cosmetic composition is provided. The meta-stable cosmetic composition includes at least one water-in-oil emulsifier having a hydrophilic-lipophilic balance (HLB) of less than 6, at least one non-ionic oil-in-water emulsifier having an HLB of greater than 9, at least one ionic surfactant; and at least one skin care active ingredient, wherein the ratio of the at least one non-ionic oil-in-water emulsifier to the at least one water-in-oil emulsifier is about 0.02 to about 2.0.

In another exemplary embodiment, a product formed from a meta-stable skin care composition is provided. The product includes at least one water-in-oil emulsifier having a hydrophilic-lipophilic balance (HLB) of less than 6, at least one non-ionic oil-in-water emulsifier having an HLB of greater than 9, at least one ionic surfactant, and at least one skin care active ingredient. The ratio of the at least one non-ionic oil-in-water emulsifier to the at least one water-in-oil emulsifier is about 0.02 to about 2.0.

The present disclosure is also directed to a method of protecting a keratinous substrate from UV radiation comprising applying onto a surface of the keratinous substrate a sunscreen product formed from a meta-stable composition.

Other features and advantages of the present invention will be apparent from the following more detailed description of the preferred embodiment which illustrates, by way of example, the principles of the invention.

DETAILED DESCRIPTION OF THE INVENTION

"Meta-stable composition," as used herein, includes a composition that remains stable at least one month in storage at 45° C.

"W/O emulsion," as used herein, includes a water phase dispersed in an oil phase, where the oil phase is a continuous phase.

"O/W emulsion," as used herein, includes oil phase dispersed in a water phase, where the water phase is a continuous phase.

"Keratinous tissue," as used herein, includes, but is not limited to, skin, hair, and nails.

"Homogenous" means substantially uniform throughout, i.e., a single phase mixture.

In the present application the term "ambient temperature" means a temperature of about 25° C.

The compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

It has been surprisingly discovered by the inventors that the compositions according to the present disclosure allow the formulation of stable and sprayable O/W emulsions, which invert very quickly into a W/O emulsion while rubbing on keratinous tissue, like the skin. Additionally, it has been surprisingly discovered by the inventors that composition has a great aesthetic profile like that of an O/W emulsion upon applying to the skin but has the final efficacy of a W/O emulsion.

W/O Emulsifiers

The oil phase present in the meta-stable cosmetic composition, according to the disclosure, includes at least one water-in-oil (W/O) emulsifier at a concentration by weight of about 0.7 to about 5.0, or alternatively about 0.7% to about 3.0%, or alternatively about 0.8% to about 2.8%, or alternatively about 0.9% to about 2.6%, based upon weight of the composition.

The at least one W/O emulsifier has an HLB of less than 6. Examples of W/O emulsifiers, include, but are not limited to, sucrose distearate, polyglyceryl-4 isostearate (and) cetyl PEG/PPG 10/1 dimethicone (and) hexyl laurate, sorbitan stearate, octyldodecyl xyloside, glyceryl stearate, PEG-30 dipolyhydroxystearate and combinations thereof.

Typically, the W/O emulsifiers (component b) are chosen from the group consisting of sorbitan esters and polyglycerol esters:

Sorbitan esters: Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Additional products of 1 to 30 mol, and preferably 5 to 10 mol, ethylene oxide onto the sorbitan esters mentioned are also suitable.

Polyplycerol esters: Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglycerly-3 Diisostearate (Isolan® PDI), Polyglyceryl-3 Methylglucose Distearate (Tego Care) 450), Polyglyceryl-3 Beeswax (Cera Bellina>), Polyglyceryl-4 Caprate (Polyglycerol Caprate T2010/90), Polyglyceryl-3 Cetyl Ether (Chimexaned NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Non-Ionic O/W Emulsifiers

The water phase in the meta-stable composition, according to the disclosure, includes at least one non-ionic oil-in-water (O/W) emulsifier at a concentration by weight of about 0.1% to about 2.0%, or alternatively about 0.2% to about 2.0%, or alternatively about 0.3% to about 1.9%, or alternatively about 0.4% to about 1.8%, based upon weight of the composition.

The at least on non-ionic O/W emulsifier has an HLB of greater than 9.

The non-ionic oil-in-water (O/W) emulsifier of the invention is preferably chosen from:
1) silicone surfactants,
2) amphiphilic lipids which are liquid at a temperature of less than or equal to 45° C. chosen from esters of at least one polyol and of at least one fatty acid including at least one saturated or unsaturated and linear or branched, and in particular unsaturated or branched, $C_8$-$C_{22}$ alkyl chain, the polyol being chosen from the group formed by polyethylene glycol including from 1 to 60 ethylene oxide units, sorbitan, glycerol possibly including from 2 to 30 ethylene oxide units, and polyglycerols including from 2 to 15 glycerol units,
3) esters of fatty acid and of sugar and ethers of fatty alcohol and of sugar,
4) surfactants which are solid at a temperature of less than or equal to 45° C. chosen from glycerol fatty esters, sorbitan fatty esters and oxyethylenated sorbitan fatty esters, ethoxylated fatty ethers and ethoxylated fatty esters,
5) block copolymers of ethylene oxide (A) and of propylene oxide (B), and the mixtures of these surfactants.
6) The silicone surfactants which can be used according to the invention are silicone compounds including at least one oxyethylene —OCH$_2$CH$_2$— chain and/or oxypropylene —OCH$_2$CH$_2$CH$_2$-chain. Mention may be made, as silicone surfactants which can be used according to the present invention, of those disclosed in documents U.S. Pat. No. 5,364,633 and U.S. Pat. No. 5,411,744, the entire contents of each of which are hereby incorporated by reference.

The silicone surfactant used according to the present invention is preferably a compound of formula (I):

in which:
$R_1$, $R_2$ and $R_3$, independently of one another, represent a $C_1$-$C_6$ alkyl radical or a —(CH$_2$)$_x$—(OCH$_2$CH$_2$)$_y$—(OCH$_2$CH$_2$CH$_2$)$_z$—OR$_4$ radical, at least one $R_1$, $R_2$ or $R_3$ radical not being an alkyl radical; $R_4$ being a hydrogen, an alkyl radical or an acyl radical;
A is an integer ranging from 0 to 200 (which range expressly includes 5, 20, 50, 100, and 150);
B is an integer ranging from 0 to 50 (which range expressly includes 5, 10, 25, 35, and 45); provided that A and B are not equal to zero at the same time;
x is an integer ranging from 1 to 6 (which range expressly includes 2, 3, 4, and 5);
y is an integer ranging from 1 to 30 (which range expressly includes 5, 10, 15, 20 and 25);
z is an integer ranging from 0 to 5 (which range expressly includes 1, 2, 3, and 4).

According to a preferred embodiment of the invention, in the compound of formula (I), the alkyl radical is a methyl radical, x is an integer ranging from 2 to 6 and y is an integer ranging from 4 to 30.

Mention may be made, as examples of silicone surfactants of formula (I), of the compounds of formula (II):

in which A is an integer ranging from 20 to 105 (which range expressly includes 30, 40, 50, 75 and 100), B is an integer ranging from 2 to 10 (which range expressly includes 3, 4, 5, 6, 7 and 8) and y is an integer ranging from 10 to 20 (which range expressly includes 12, 14, 16, and 18).

Mention may also be made, as examples of silicone surfactants of formula (I), of the compounds of formula (III):

$$H-(OCH_2CH_2)_{y'}-(CH_2)_3-[(CH_3)_2SiO]_{A'}-(CH_2)_3-(OCH_2CH_2)_{y'}-OH \quad (III)$$

in which A' and y are integers ranging from 10 to 20 (which range expressly includes 12, 14, 16, and 18).

Use may in particular be made, as silicone surfactants, of those sold by Dow Corning under the names DC 5329, DC 7439-146, DC 2-5695 and Q4-3667. The compounds DC 5329, DC 7439-146 and DC 2-5695 are compounds of formula (II) where respectively A is 22, B is 2 and y is 12; A is 103, B is 10 and y is 12; A is 27, B is 3 and y is 12.

2) The esters of fatty acid and of sugar can be chosen in particular from the group including esters or mixtures of esters of $C_8$-$C_{22}$ fatty acid and of sucrose, of maltose, of glucose or of fructose and esters or mixtures of esters of $C_{14}$-$C_{22}$ fatty acid and of methylglucose.

The $C_8$-$C_{22}$ or $C_{14}$-$C_{22}$ fatty acids forming the fatty unit of the esters which can be saturated or unsaturated linear alkyl chain having from 8 to 22 or from 14 to 22 carbon atoms respectively (which ranges expressly include 10, 12, 16, 18 and 20 as appropriate). The fatty unit of the esters can be chosen in particular from stearates, behenates, arachidonates, palmitates, myristates, laurates, caprates and their mixtures. Stearates are preferably used.

Mention may be made, as examples of esters or of mixtures of esters of fatty acid and of sucrose, of maltose, of glucose or of fructose, of sucrose monostearate, sucrose distearate, sucrose tristearate and their mixtures, such as the products sold by Croda under the name Crodesta F110 and F160 having respectively an HLB (Hydrophilic Lipophilic Balance) of 11 and 16; and, as examples of esters or of mixtures of esters of fatty acid and of methylglucose, of the distearate of methylglucose and of polyglycerol-3, sold by Goldschmidt under the name of Tego-care 450. Mention may also be made of glucose or maltose monoesters, such as methyl 0-hexadecanoyl6-D-glucoside and 0-hexadecanoyl-6-D-maltoside.

The ethers of fatty alcohol and of sugar which can be chosen in particular from the group including ethers or mixtures of ethers of $C_8$-$C_{22}$ fatty alcohol and of glucose, of maltose, of sucrose or of fructose and ethers or mixtures of ethers of $C_{14}$-$C_{22}$ fatty alcohol and of methylglucose. They are in particular alkylpolyglucosides.

The $C_8$-$C_{22}$ or $C_{14}$-$C_{22}$ fatty alcohols forming the fatty unit of the ethers which can be used in the nanoemulsion of the invention include a saturated or unsaturated linear alkyl chain having from 8 to 22 or from 14 to 22 carbon atoms respectively (which ranges expressly include 10, 12, 16, 18 and 20 as appropriate). The fatty unit of the ethers can be chosen in particular from the decyl, cetyl, behenyl, arachidyl, stearyl, palmityl, myristyl, lauryl, capryl or hexadecanoyl units and their mixtures, such as cetearyl.

Mention may be made, as examples of ethers of fatty alcohol and of sugar, of alkylpolyglucosides, such as decylglucoside and laurylglucoside, sold, for example, by Henkel under the respective names of Plantaren 2000 and Plantaren 1200, cetostearyl-glucoside, optionally as a mixture with cetostearyl alcohol, sold, for example, under the name Montanov 68 by Seppic, under the name Tego-care CG90 by Goldschmidt and under the name Emulgade KE3302 by Henkel, and arachidylglucoside, for example in the form of the mixture of arachidyl and behenyl alcohols and of arachidylglucoside sold under the name Montanov 202 by Seppic.

Use is more particularly made, as non-ionic amphiphilic lipid of this type, of sucrose monostearate, sucrose distearate, sucrose tristearate and their mixtures, the distearate of methylglucose and of polyglycerol-3, and alkylpolyglucosides.

The glycerol fatty esters can be chosen in particular from the group including the esters formed of at least one acid including a saturated linear alkyl chain having from 16 to 22 carbon atoms (which range expressly includes 18 and 20) and of 1 to 10 glycerol units (which range expressly includes 2, 3, 4, 5, 6, 7, 8 and 9). Use may be made of one or more of these glycerol fatty esters in the nanoemulsion of the invention.

The sorbitan fatty esters which can be chosen in particular from the group including esters of $C_{16}$-$C_{22}$ fatty acid and of sorbitan and oxyethylenated esters of $C_{16}$-$C_{22}$ fatty acid and of sorbitan. They are formed of at least one fatty acid including at least one saturated linear alkyl chain, having respectively from 16 to 22 carbon atoms, and of sorbitol or of ethoxylated sorbitol. The oxyethylenated esters generally include from 1 to 100 ethylene oxide units and preferably from 2 to 40 ethylene oxide (EO) units.

These esters can be chosen in particular from stearates, behenates, arachidates, palmitates and their mixtures.

The ethoxylated fatty ethers which are solid at a temperature of less than or equal to 45° C. which can be used as non-ionic amphiphilic lipids in the nanoemulsion according to the invention are preferably ethers formed of 1 to 100 ethylene oxide units and of at least one fatty alcohol chain having from 16 to 22 carbon atoms. The fatty chain of the ethers can be chosen in particular from the behenyl, arachidyl, stearyl or cetyl units and their mixtures, such as cetearyl. Mention may be made, as examples of ethoxylated fatty ethers, of the ethers of behenyl alcohol including 5, 10, 20 and 30 ethylene oxide units.

The ethoxylated fatty esters are esters formed of 1 to 100 ethylene oxide units and of at least one fatty acid chain including from 16 to 22 carbon atoms. The fatty chain of the esters can be chosen in particular from the stearate, behenate, arachidate or palmitate units and their mixtures.

3) The block copolymers of ethylene oxide and of propylene oxide, which can be used as non-ionic amphiphilic lipids in the nanoemulsion according to the invention can be chosen in particular from the block copolymers of formula (IV):

$$HO(C_2H_4O)_x(C_3H_6O)_y(C_2H_4O)_zH \quad (IV)$$

in which x, y and z are integers such that x+z ranges from 2 to 100 (which range expressly includes 5, 10, 20, 40, 60, and 80) and y ranges from 14 to 60 (which range expressly includes 16, 18, 20, 30, 40 and 50), and their mixtures and more particularly from the block copolymers of formula (V) having an HLB ranging from 9 to 16 (which range expressly includes 4, 6, 8, 10, 12, and 14).

Ionic Surfactants

The water phase in the meta-stable composition, according to the disclosure, includes at least one ionic surfactant. The ionic surfactant may be an anionic surfactant or a cationic surfactant. The ionic surfactant is provided at a concentration by weight of about 0.1% to about 1.0%, or alternatively about 0.2% to about 0.9%, or alternatively about 0.3% to about 0.8%, based upon weight of the composition. The nature of the ionic surfactants is more important with respect to stability and the power to induce a spontaneous phase inversion of the emulsion when applied to skin.

Anionic surfactants useful as ionic surfactants in the present composition include anionic amphiphilic lipids which can be chosen from: 1) mixed esters of fatty acid or of fatty alcohol, of carboxylic acid and of glycerol, 2) alkyl ether citrates, 3) alkenyl succinates chosen from alkoxylated alkenyl succinates, alkoxylated glucose alkenyl succinates and alkoxylated methylglucose alkenyl succinates, and 4) phosphoric acid fatty esters.

Examples of the mixed esters of fatty acid or of fatty alcohol, of carboxylic acid and of glycerol which can be used as anionic amphiphilic lipids in the composition, according to the invention, can be chosen in particular from the group including mixed esters of fatty acid or of fatty alcohol having an alkyl chain including from 8 to 22 carbon atoms and of α-hydroxy acid and/or of succinic acid with glycerol. The α-hydroxy acid can be, for example, citric acid, lactic acid, glycolic acid, malic acid and their mixtures.

Examples of the alkyl chain of the fatty acids or alcohols from which the mixed esters which can be used as anionic surfactants in the composition of the invention derive can be saturated or unsaturated and linear or branched. It can, in particular, be stearate, isostearate, linoleate, oleate, behenate, arachidonate, palmitate, myristate, laurate, caprate, isostearyl, stearyl, linoleyl, oleyl, behenyl, myristyl, lauryl and capryl chains and their mixtures.

Mention may be made, as examples of mixed esters which can be used in the composition of the invention, of the mixed ester of glycerol and of the mixture of citric, lactic, linoleic and oleic acids (INCI name: Glyceryl citrate/lactate/linoleate/oleate) sold by Hills under the name Imwitor 375; the mixed ester of succinic acid and of isostearyl alcohol with glycerol (INCI name: Isostearyl diglyceryl succinate) sold by Huls under the name Imwitor 780 K; the mixed ester of citric acid and of stearic acid with glycerol (INCI name: Glyceryl stearate citrate) sold by Hills under the name Imwitor 370; or the mixed ester of lactic acid and of stearic acid with glycerol (INCI name: Glyceryl stearate lactate) sold by Danisco under the name Lactodan B30 or Rylo LA30.

Examples of the alkyl ether citrates, which can be used as anionic surfactants in the composition, according to the invention, can be chosen in particular from the group including the monoesters, diesters or triesters formed by citric acid and at least one oxyethylenated fatty alcohol, including a saturated or unsaturated and linear or branched alkyl chain having from 8 to 22 carbon atoms and including from 3 to 9 ethoxylated groups, and their mixtures. This is because it is possible to use a mixture of one or more of these citrates in the composition of the invention.

These citrates can be chosen, for example, from the mono-, di- and triesters of citric acid and of ethoxylated lauryl alcohol, including from 3 to 9 ethoxylated groups, sold by Witco under the name Witconol EC, in particular Witconol EC 2129, which is predominantly a dilaureth-9 citrate, and Witconol EC 3129, which is predominantly a trilaureth-9 citrate.

The alkyl ether citrates used as anionic surfactants lipids are preferably employed in the form neutralized to a pH of approximately 7, the neutralizing agent being chosen from inorganic bases, such as sodium hydroxide, potassium hydroxide or ammonia, and organic bases, such as mono-, di- and triethanolamine, aminomethylpropane-1,3-diol, N-methylglucamine or basic amino acids, such as arginine and lysine, and their mixtures.

The alkenyl succinates which can be used as anionic surfactants in the composition of the invention are in particular ethoxylated and/or propoxylated derivatives and they are preferably chosen from the compounds of formulae (V) or (VI):

HOOC—(HR)C—CH$_2$—COO-E (V)

HOOC—(HR)C—CH$_2$—COO-E-O—CO—CH$_2$—C(HR')—COOH (VI)

in which: the R and R' radicals are chosen from linear or branched alkyl radicals including from 6 to 22 carbon atoms (which range expressly includes 10, 12, 14, 16, 18, and 20), E is chosen from oxyethylene chains of formula $(C_2H_4O)_n$ in which n ranges from 2 to 100 (which range expressly includes 10, 20, 40, 60, 80 and 90), oxypropylene chains of formula $(C_3H_6O)_{n'}$, in which n' ranges from 2 to 100 (which range expressly includes 5, 10, 20, 30, 40, 50, 60, 70, 80 and 90), random or blocked copolymers including 5 oxyethylene chains of formula $(C_2H_4O)_n$ and oxypropylene chains of formula $(C_3H_6O)_{n'}$ such that the sum of n and n' ranges from 2 to 100 (which range expressly includes 5, 10, 20, 30, 40, 50, 60, 70, 80 and 90), oxyethylenated and/or oxypropylenated glucose groups including, on average, from 4 to 100 oxyethylene and/or oxypropylene units distributed over all the hydroxyl functional groups, or oxyethylenated and/or oxypropylenated methylglucose groups including, on average, from 4 to 100 oxyethylene and/or oxypropylene units distributed over all the hydroxyl functional groups (which ranges expressly include 5, 10, 20, 30, 40, 50, 60, 70, 80 and 90).

In the formulae (V) and (VI), n and n' are mean values and are therefore not necessarily integers. The choice is advantageously made, for n, of a value ranging from 5 to 60 and more preferably still from 10 to 30.

The R and/or R' radical is advantageously chosen from linear alkyl radicals including from 8 to 22 and preferably from 14 to 22 carbon atoms (which ranges expressly include 10, 12, 14, 16, 18 and 20 carbons as appropriate). Preferably, it can be, for example, the hexadecenyl radical, including 16 carbon atoms, or the octadecenyl radical, including 18 carbon atoms.

The compounds of formulae (V) and (VI) described above in which E is chosen from oxyethylene chains, oxypropylene chains and copolymers including oxyethylene chains and oxypropylene chains can be prepared in accordance with the description which is given in documents WO-A-94/00508, EP-A-1 071 99 and GB-A-2 131 820, the entire contents of each of which are incorporated herein by reference.

The acid functional group —COOH of the anionic surfactants of formulae (V) and (VI) is generally found in the composition of the invention in the form neutralized by a neutralizing agent, the neutralizing agent being chosen, for example, from inorganic bases, such as sodium hydroxide, potassium hydroxide or ammonia, and organic bases, such as mono-, di- and triethanolamine, aminomethylpropane-1, 3-diol, N-methylglucamine or basic amino acids, such as arginine and lysine, and their mixtures.

Examples of the phosphoric acid fatty esters and their oxyethylenated derivatives, which can be used as anionic surfactants in the compositions, according to the invention, can be chosen in particular from the group including the esters formed of phosphoric acid and of at least one alcohol including a saturated or unsaturated and linear or branched alkyl chain having from 8 to 22 carbon atoms (which range expressly includes 10, 12, 14, 16, 18 and 20) and the esters formed of phosphoric acid and of at least one ethoxylated alcohol including a saturated or unsaturated and linear or branched alkyl chain having from 8 to 22 carbon atoms (which range expressly includes 10, 12, 14, 16, 18 and 20) and including from 2 to 40 oxyethylene groups (which range expressly includes 4, 6, 8, 10, 12, 14, 16, 18, 20 and 30), their salts and their mixtures. This is because it is possible to use a mixture of one or more of these phosphoric acid esters in the composition of the invention.

These esters can be chosen in particular from esters of phosphoric acid and of $C_9$-$C_{15}$ alcohols or their salts, such as the potassium salt of $C_9$-$C_{15}$ alkyl phosphate sold under the name Arlatone MAP by ICI; esters of phosphoric acid and of stearyl and/or isostearyl alcohols, such as the phosphate of stearylisostearyl alcohols (INCI name: Octyldecyl phosphate) sold under the name Hostaphat CG120 by Hoechst Celanese; esters of phosphoric acid and of cetyl alcohol, and their oxyethylenated derivatives, such as the product sold under the name Crodafos CES (mixture of cetearyl alcohol, of dicetyl phosphate and of ceteth-10 phosphate) by Croda; or esters of phosphoric acid and of tridecyl alcohol, and their oxyethylenated derivatives, such as the product sold under the name Crodafos T10 (INCI name: Trideceth-10 phosphate) by Croda. The oxyethylenated derivatives of phosphoric acid and of fatty alcohol can be prepared in accordance with the description given in Patent Application WO-A-96/14145, the entire contents of which is incorporated in the present application by reference.

Additional anionic surfactants which can be used in the compositions of the invention are preferably chosen from: alkaline salts of dicetyl and dimyristyl phosphate; alkaline salts of cholesterol sulfate; alkaline salts of cholesterol phosphate; lipoamino acids and their salts, such as mono- and disodium acylglutamates, for instance the disodium salt of N-stearoyl-L-glutamic acid sold under the name Acylglutamate HS21 by Ajinomoto; sodium salts of phosphatidic acid; phospholipids; alkylsulfonic derivatives, in particular of formula (VII):

(VII)

in which R represents $C_{16}$-$C_{22}$ alkyl radicals, in particular the $C_{16}H_{33}$ and $C_{18}H_{37}$ radicals taken as a mixture or separately, and M is an alkali metal or an alkaline earth metal, such as sodium; and their mixtures.

Examples of particularly suitable ionic surfactants, include, but are not limited to, ionic surfactant is chosen from sodium stearoyl glutamate, potassium cetyl phosphate, disodium stearoyl glutamate, and combinations thereof. The at least one ionic surfactant can be an anionic surfactant or cationic surfactant.

Cationic surfactants useful as ionic surfactants in the present composition include cationic amphiphilic lipids that are preferably chosen from the group formed by quaternary ammonium salts, fatty amines and salts thereof.

The quaternary ammonium salts are, for example: those which have the following general formula (VIII):

(VIII)

in which the radicals $R_1$ to $R_4$, which may be identical or different, represent a linear or branched aliphatic radical containing from 1 to 30 carbon atoms (which range expressly includes 2, 4, 6, 8, 10, 15, 20, and 25), or an aromatic radical such as aryl or alkylaryl. The aliphatic radicals may contain heteroatoms, such as in particular, oxygen, nitrogen, sulfur or halogens. The aliphatic radicals are, for example, chosen from the alkyl, alkoxy, polyoxy ($C_2$-$C_6$)alkylene, alkylamide, ($C_{12}$-$C_{22}$) alkylamido ($C_2$-$C_6$) alkyl, ($C_{12}$-$C_{22}$) alkyl acetate or hydroxyalkyl radicals containing from about 1 to 30 carbon atoms (which range expressly includes 2, 4, 6, 8, 10, 15, 20, and 25); X is an anion chosen from the group including halides, phosphates, acetates, lactates, ($C_2$-$C_6$) alkyl sulfates and alkyl- or alkylarylsulfonates, the quaternary ammonium salts of imidazolinium, such as, for example, that of the following formula (IX):

(IX)

in which $R_5$ represents an alkenyl or alkyl radical containing from 8 to 30 carbon atoms (which range expressly includes 10, 12, 14, 16, 18, 20, 22 and 26) which are, for example, derived from tallow fatty acids, $R_6$ represents a hydrogen atom, a $C_1$-$C_4$ alkyl radical or an alkenyl or alkyl radical containing from 8 to 30 carbon atoms (which range expressly includes 10, 12, 14, 16, 18, 20, 22 and 26), $R_7$ represents a $C_1$-$C_4$ alkyl radical, $R_8$ represents a hydrogen atom, a $C_1$-$C_4$ alkyl radical, X is an anion chosen from the group including the halides, phosphates, acetates, lactates, alkyl sulfates, alkyl- or alkylarylsulfonates. Preferably, $R_5$ and $R_6$ designate a mixture of alkenyl or alkyl radicals containing from 12 to 21 carbon atoms which are, for example, derived from tallow fatty acids, $R_7$, designates methyl and $R_8$ designates hydrogen. Such a product is, for example, marketed under the name "REWOQUAT W 75" by the company REWO. Among the quaternary ammonium salts of formula (VIII), there are preferred, on the one hand, the tetraalkylammonium chlorides, such as, for example, the dialkyldimethylammonium or alkyltrimethylammonium chlorides, in which the alkyl radical contains from about 12 to 22 carbon atoms (which range expressly includes 14, 16, 18, and 22), in particular the behenyltrimethylammonium, distearyldimethylammonium, cetyltrimethylammonium and benzyldimethylstearyl-ammonium chlorides or alternatively, on the other hand, the stearamidopropyldimethyl (myristyl acetate)ammonium chloride marketed under the name "CERAPHYL 70" by the company VAN DYK. The behenyltrimethylammonium chloride is the quaternary ammonium salt most particularly preferred. The quaternary diammonium salts of formula (X):

(X)

in which $R_9$ designates an aliphatic radical containing from about 16 to 30 carbon atoms, $R_{10}$, $R_{11}$, $R_{12}$, $R_{13}$ and the saturated or unsaturated, linear or branched $C_1$-$C_6$ hydrocarbon radicals $R_{22}$, the hydrogen atom, $R_{17}$, $R_{19}$ and $R_{21}$, which are identical or different, are chosen from the saturated or unsaturated, linear or branched $C_7$-$C_{21}$ hydrocarbon radicals; n, p and r, which are identical or different, are integers having values from 2 to 6 (which range expressly includes 3, 4, and 5); y is an integer having a value from 1 to 10 (which range expressly includes 2, 3, 4, 5, 6, 7, 8, and 9); x and z, which are identical or different, are integers having values from 0 to 10 (which range expressly includes 1, 2, 3, 4, 5, 6, 7, 8, and 9); $X^-$ is an organic or inorganic, simple or complex anion (such as those described herein above and below); with the proviso that the sum x+y+z has a value from 1 to 15, that when x has a value of 0, then $R_{16}$ designates $R_{20}$, and that when z has a value of 0, then $R_{18}$ designates $R_{22}$. The alkyl radicals $R_{15}$ may be linear or branched and more particularly linear. Preferably, $R_{15}$ designates a methyl, ethyl, hydroxyethyl or dihydroxypropyl radical and more particularly a methyl or ethyl radical. Advantageously, the sum x+y+z has a value from 1 to 10 (which range expressly includes 2, 3, 4, 5, 6, 7, 8 and 9). When $R_{16}$ is a hydrocarbon radical $R_{20}$, it may be long and may have from 12 to 22 carbon atoms (which range expressly includes 14, 16, 18, and 20), or may be short and may have from 1, 2, or 3 carbon atoms. $R_{14}$, which are identical or different, are chosen from hydrogen or an alkyl radical containing from 1, 2, 3, or 4 carbon atoms, and X is an anion chosen from the group including the halides, acetates, phosphates, nitrates and methyl sulfates. Such quaternary diammonium salts include, in particular, propanetallowdiammonium dichloride.

The quaternary ammonium salts containing at least one ester functional group which can be used, according to the invention, are, for example, those of the following formula (XI):

in which: $R_{15}$ is chosen from $C_1$-$C_6$ alkyl radicals and $C_1$-$C_6$ hydroxyalkyl or dihydroxyalkyl radicals; $R_{16}$ is chosen from:
the radical the saturated or unsaturated, linear or branched $C_1$-$C_{22}$ hydrocarbon radicals $R_{20}$, the hydrogen atom, $R_{18}$ is chosen from:
the radical the saturated or unsaturated, linear or branched $C_1$-$C_6$ hydrocarbon radicals $R_{22}$, the hydrogen atom, $R_{17}$, $R_{19}$ and $R_{21}$, which are identical or different, are chosen from the saturated or unsaturated, linear or branched $C_7$-$C_{21}$ hydrocarbon radicals; n, p and r, which are identical or different, are integers having values from 2, 4, 5, or 6; y is an integer having a value from 1 to 10 (which range expressly includes 2, 3, 4, 5, 6, 7, 8, and 9); x and z, which are identical or different, are integers having values from 0 to 10 (which range expressly includes 1, 2, 3, 4, 5, 6, 7, 8, and 9); $X^-$ is an organic or inorganic, simple or complex anion (such as those described hereinabove and below); with the proviso that the sum x+y+z has a value from 1 to 15, that when x has a value of 0, then $R_{16}$ designates $R_{20}$, and that when z has a value of 0, then $R_{18}$ designates $R_{22}$. The alkyl radicals $R_{15}$ may be linear or branched and more particularly linear. Preferably, $R_{15}$ designates a methyl, ethyl, hydroxyethyl or dihydroxypropyl radical and more particularly a methyl or ethyl radical. Advantageously, the sum x+y+z has a value from 1 to about 10. When $R_{16}$ is a hydrocarbon radical $R_{20}$, it may be long and may have from 12 to 22 carbon atoms (which range expressly includes 14, 16, 18 and 20), or may be short and may have from 1, 2, or 3 carbon atoms. When $R_{18}$ is a hydrocarbon radical $R_{22}$, it preferably has 1 to 3 carbon atoms. Advantageously, $R_{17}$, $R_1$, $R_9$ and $R_{21}$, which are identical or different, are chosen from saturated or unsaturated, linear or branched $C_{11}$-$C_{21}$ hydrocarbon radicals, and more particularly from saturated or unsaturated, linear or branched $C_{11}$-$C_{21}$ alkyl and alkenyl radicals. Preferably, x and z, which are identical or different, have a value of 0 or 1. Advantageously, y is equal to 1. Preferably, n, p and r, which are identical or different, have a value of 2 or 3 and, still more particularly, are equal to 2.

In formula (XI), the anion is preferably a halide (chloride, bromide or iodide) or an alkyl sulfate, more particularly methyl sulfate. It is, however, possible to use methanesulfonate, phosphate, nitrate, tosylate, an organic acid-derived anion, such as acetate or lactate or any other anion compatible with ammonium containing an ester functional group. The anion $X^-$ is still more particularly chloride or methyl sulfate.

Use is more particularly made of the ammonium salts of formula (XI) in which: $R_{15}$ designates a methyl or ethyl radical, x and y are equal to 1; z is equal to 0 or 1; n, p and r are equal to 2; $R_{16}$ is chosen from: the radical the methyl, ethyl or $C_{14}$-$C_{22}$ hydrocarbon radicals; the hydrogen atom $R_{18}$ is chosen from: the radical the hydrogen atom; $R_{17}$, $R_{19}$ and $R_{21}$, which are identical or different, are chosen from saturated or unsaturated, linear or branched $C_{13}$-$C_{17}$ hydrocarbon radicals and preferably from saturated or unsaturated, linear or branched $C_{13}$-$C_{17}$ alkyl and alkenyl radicals. Advantageously, the hydrocarbon radicals are linear.

There may be mentioned, for example, as compounds of formula (XI), the salts (chloride or methyl sulfate in particular) of diacyloxyethyldimethylammonium, of diacyloxyethyl-hydroxyethylmethylammonium, of monoacyloxyethyl-dihydroxyethylmethylammonium, of triacyloxyethylmethylammonium, of monoacyloxyethylhydroxyethyldimethylammonium and mixtures thereof. The acyl radicals preferably have 14 to 18 carbon atoms and are more particularly obtained from a vegetable oil, such as palm oil or sunflower oil. When the compound contains several acyl radicals, the latter may be identical or different. These products are obtained, for example, by direct esterification of triethanolamine, of triisopropanolamine, of alkyldiethanolamine or of alkyldiisopropanolamine which are optionally oxyalkylenated on fatty acids or on mixtures of fatty acids of plant or animal origin or by transesterification of methyl esters thereof. This esterification is followed by quaternization with the aid of an alkylating agent, such as an alkyl (preferably methyl or ethyl) halide, a dialkyl (preferably methyl or ethyl) sulfate, methyl methanesulfonate, methyl para-toluenesulfonate, or glycol or glycerol chlorohydrin. Such compounds are, for example, marketed under the names DEHYQUART by the company HENKEL, STEPANQUAT by the company STEPAN, NOXAMIUM by the company CECA, REWOQUAT WE 18 by the company REWO-WITCO.

The composition, according to the invention, when it contains ammonium salts, preferably contains a mixture of quaternary ammonium mono-, di- and triester salts, with a majority by weight of diester salts.

As a mixture of ammonium salts, there may be used, for example, the mixture containing 15% to 30% by weight of acyloxyethyldihydroxyethylmethylammonium methyl sulfate, 45% to 60% of diacyloxyethyl-hydroxyethylmethylammonium methyl sulfate and 15% to 30% of triacyloxyethylmethylammonium methyl sulfate, acyl radicals having from 14 to 18 carbon atoms and being obtained from optionally partially hydrogenated palm oil.

It is also possible to use the ammonium salts containing at least one ester functional group which are described in patents, U.S. Pat. No. 4,874,554 and U.S. Pat. No. 4,137,180, the entire contents of each of which are hereby incorporated by reference.

The combined concentration by weight of the at least one water-in-oil emulsifier, the at least one non-ionic oil-in-water emulsifier and the at least one ionic surfactant does not exceed about 6% by weight or alternatively does not exceed 4% by weight, based on the total weight of the composition.

The composition includes an oil phase containing surfactants. The surfactants in the oil phase comprise less than 40% by weight, less than 35% by weight, less that 31% by weight, less than about 30% by weight of the oil phase, less than 20%, less than about 15% by weight of the oil phase, or alternatively less than about 10% by weight of the oil phase.

Skin Care Active Ingredient

The aqueous phase or the oil phase, depending on the nature of the active ingredient, includes an active ingredient. The meta-stable cosmetic composition, according to the disclosure, includes an active ingredient at a concentration, by weight, of about 1% to about 40%, or alternatively about 1.5% to about 35%, or alternatively about 2% to about 30%, based upon weight of the composition. The active ingredient may include, dermatological active agents, emollients, humectants, hydrating active agent or any other suitable skin care active component.

Dermatological Active Ingredient

In one embodiment, the skin care active ingredient includes dermatological active ingredients. In this embodiment, the meta-stable cosmetic or skin composition according to the present invention may include dermatological active agents, such as, but not limited to anti-aging and/or anti-oxidation agents. Examples of dermatological active agents include free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the meta-stable cosmetic composition (i.e., aqueous and/or fatty (oil) phase.)

The meta-stable cosmetic composition of the present invention may also contain active ingredients for artificially tanning and/or browning the skin (self-tanning agents) and more particularly dihydroxyacetone (DHA). They are preferably present in amounts ranging from 0.1% to 10% by weight relative to the total weight of the composition.

The dermatological active ingredient is typically present in an amount of from about 1.0% to about 40% by weight, such as from about 1.5% to about 35% by weight, and from about 2.0% to about 30% by weight, based on the total weight of the composition.

Emollient

In one embodiment, the skin care active ingredient includes emollient. In this embodiment, the meta-stable cosmetic or skin composition according to the present invention may include polar and/or non-polar emollients. Suitable polar emollients include, but are not limited to, polyol esters and polyol ethers such as linear or branched chained polyglycerol esters and polyglycerol ethers. Particularly suitable emollients for use as the first emollient include caprylicicapric triglyceride, isopropyl myristate, PPG-3 myristyl ether, isopropyl palmitate, dibutyl adipate, propyleneglycol dicaprylate/dicaprate, cocoglyceride, cetearyl isononanoate, isopropyl myristate, isodecyl neopentanoate, tridecyl neopcntanoate, $C_{12-15}$ alkyl benzoate, isopropyl lauroyl sarsosinate, phenethyl benzoate and mixtures thereof. Other suitable emollients include any oil soluble emollients having high or medium polarity moieties.

The polar emollient may be present at a concentration of, by weight of the entire composition, between about 1.0% and about 30%, between about 7.0% and about 12.0%, between about 9.0% and about 11.0%, or any suitable combination, sub-combination, range, or sub-range thereof.

Suitable non-polar emollients may include, but are not limited to, non-polar hydrocarbon, such as esters, linear or branched, or chained hydrocarbons. Non-limiting examples of such emollients may include paraffins, isoparaffins, mineral oil, silicone oils, dimethicone, isohexadecane, isododecane, diethylhexyl cyclohexane, and mixtures thereof. Particularly suitable emollients for use as the second emollient include one or more of dicaprylyl ether, isododecane, hydrocarbon, dimethicone and mixtures thereof. In other embodiments, the emollient includes non-silicone oils and dimethicone. In other embodiments, the second emollient includes dimethicone with one or more additional non-polar emollients.

The non-polar emollient may be present at a concentration of, by weight of the entire composition, between about 1.0% and about 30%, between about 5.0% and about 12.0%, between about 9.0% and about 11.0%, or any suitable combination, sub-combination, range, or sub-range thereof.

Humectant

In one embodiment, the skin care active ingredient includes humectant. In this embodiment, the humectant present in the meta-stable cosmetic composition according to the present invention includes glycerin, sodium hyaluronate, panthenol, urea, hydroxyethyl urea, PEG/PPG/polybutylene glycol-8/5/3 glycerin, hydrolyzed hyaluronic acid, niacinamide, mannose, myristyl malate phosphonic acid, biosaccharide gum, and combinations thereof.

The humectant is advantageously present at a concentration, by weight, of about 0.01% to about 30%, or alternatively 0.1% to alternatively about 25%, or alternatively about 1% to about 20%, based upon weight of the meta-stable cosmetic composition.

Hydrating Active Ingredient

In one embodiment, the skin care active ingredient includes hydrating active ingredient. In this embodiment, the hydrating active ingredient is at a concentration, by weight, of about 0.1% to about 90%, or alternatively about 10% to about 90% or alternatively about 25% to about 80%, based upon weight of the composition. In one embodiment, the hydrating active ingredient is aloe vera or INCI *Aloe Barbadensis* Leaf Juice.

In one embodiment, the *Aloe Barbadensis* LeafJuice used is 80% *Aloe Vera* Gel (1×) Decolorized from Terry Laboratories, Melbourne, Fla.

Mattifier

The meta-stable cosmetic composition of the present invention optionally includes at least one mattifier. The mattifier includes acrylate copolymer, Nylon-12, polyamides, and combinations thereof.

Gelling Agent

The gelling agent present in the meta-stable cosmetic composition according to the present disclosure includes but not limited to carbomer, acrylates/C10-30 alkyl acrylate crosspolymer, and combinations thereof. A suitable example of carbomer includes Carbomer, available from 3V of Sigma. Georgetown, S.C. Suitable example of acrylates/C10-30 alkyl acrylate crosspolymer includes CARBOPOL® Ultrez 20 Polymer, available from LUBRIZOL, Cleveland. Ohio.

The gelling agent is advantageously present at a concentration, by weight, of about 0.01% to about 5%, or alternatively about 0.05% to about 4%, or alternatively about 0.5% to about 3.0% based upon weight of the composition.

Thickener

The at least one thickener present in the meta-stable cosmetic composition according to the present disclosure includes but not limited to acrylates/C10-30 alkyl acrylate crosspolymer, sodium acrylate/sodium acryloyldimethyl taurate copolymer, acrylamide/sodium acryloyldimethyltaurate copolymer, ammonium polyacryloyldimethyl taurate, ammonium acryloydimethyl taurate/VP copolymer, carbomer, xanthan gum, sodium polyacrylate, and combinations thereof.

The thickener is advantageously present at a concentration, by weight, of about 0.01% to about 2%, or alternatively about 0.08% to about 1.5%, or alternatively about 0.1% to about 1.0%, based upon weight of the meta-stable cosmetic composition.

In one embodiment, the ammonium acryloyldimethyltaurate/steareth-8 methacrylate copolymer is ARISTOFLEX SNC, available from Clariant International Ltd.

The thickener is advantageously present at a concentration, by weight, of about 0.1% to about 5%, or alternatively about 0.5% to about 4%, or alternatively about 0.8% to about 3.5% based upon weight of the composition.

Arginine

The meta-stable cosmetic composition further comprises arginine to serve as a neutralizer and to enhance moisture retention.

Arginine is advantageously present at a concentration, by weight, of about 0.05% to about 1.5%, or alternatively about 0.1% to about 1.3%, or alternatively about 0.2% to about 1.2% based upon weight of the composition.

Film Forming Polymers

Compositions of the present invention may include a film-forming polymer to enhance film formation and provide some water resistance. By "film-forming polymer," it is meant a polymer that when dissolved in the composition, permits a continuous or semi-continuous film to be formed when the composition is spread onto, e.g., smooth glass, and the liquid vehicle is allowed to evaporate. As such, the polymer should dry on the glass in a manner in which over the area which it is spread should be predominantly continuous, rather than forming a plurality of discrete, island-like structures. Generally, the films formed by applying compositions on the skin according to embodiments of the invention described herein, are less than, on average, about 100 microns in thickness, such as less than about 50 microns.

Suitable film-forming polymers include natural polymers, such as polysaccharides or proteins and synthetic polymers, such as polyesters, polyacrylics, polyurethanes, vinyl polymers, polysulfonates, polyureas, polyoxazolines, and the like. Specific examples of film-forming polymers include, for example, acrylic homopolymers or copolymers with hydrophobic groups such as acrylate/ocylacrylamide copolymers including DERMACRYL 79 available from Akzo Chemical of Bridgewater, N.J.; dimethicone/acrylates dimethicone copolymer available as X-22-8247D from Shin-Etsu of Japan; hydrogenated dimer dilinoleyl/dimethylcarbonate copolymer, available from Cognis Corporation of Ambler, Pa. as COSMEDIA DC; copolymer of vinylpyrrolidone and a long-chain a-olefin, such as those commercially available from ISP Specialty Chemicals of Wayne, N.J. as GANEX V220; vinylpyrrolidone/tricontanyl copolymers available as GANEX WP660 also from ISP; water-dispersible polyesters, including sulfopolyesters such those commercially available from Eastman Chemical as EASTMAN AQ 38S. In certain embodiments, the film-forming polymer is water insoluble, but is rendered soluble upon exposure to alkalinity in order to facilitate removal from the skin upon washing with soap.

The polymers used according to the present invention may be water-soluble, that is to say they are soluble in water, and are non-ionic or neutral.

The water-soluble neutral polymers used according to the invention are chosen from the polymers described below and mixtures thereof.

A) homopolymers and copolymers of ethylene oxide, having a molar mass equal to or greater than 10,000 g/mol and preferably ranging from 10,000 g/mol to Ser. No. 10/000,000 g/mol. These ranges expressly include 20,000, 50,000, 100,000, 200,000, 500,000, 1,000,000 and 5,000,000 g/mol. They may be chosen from:

(1) poly(ethylene oxides) having the following formula (XII):

$$R\text{---}(CH_2\text{---}CH_2\text{---}O)_n\text{---}R' \qquad (XII)$$

in which R is chosen from the hydroxyl (OH), methoxy (OCH$_3$) and amine (NH$_2$) groups, R' is a methyl (CH$_3$) group or a hydrogen, and n is a number ranging from 220 to 230,000. This range expressly includes 500, 1,000, 5,000, 10,000, 100,000 and 200,000. (2) copolymers of ethylene oxide and of one or more oxyalkylenated monomers having the following formula (XIII):

$$\text{---}(CHR\text{---}CHR'\text{---}O)\text{---} \qquad (XIII)$$

in which R and R', independently of each other, are hydrogen or an alkyl group including from 1 to 7 carbon atoms, at least one of R or R' being an alkyl group. This range expressly includes 2, 3, 4, 5, and 6 carbons.

Among the homopolymers and copolymers of ethylene oxide, there may be mentioned, in particular, the products marketed under the names Polyox Coagulant (molar mass of about $5 \times 10^6$ g/mol) (INCI name: PEG-115M) and Polyox WSR N-60K CG (INCI name: PEG-45M) (molar mass of about $2 \times 10^6$ g/mol) by the company Amerchol, as well as the product marketed under the name Carbowax 20M (INCI name: PEG-350) (molar mass of about $2 \times 10^7$ g/mol) by the company Union Carbide.

B) polyvinyl alcohols, in particular, those having an average molar mass ranging from 10,000 g/mol to 500,000 g/mol. This range expressly includes 20,000, 50,000, 100,000, 200,000, 300,000 and 400,000 g/mol. These are compounds represented by the following formula (XIV):

(XIV)

in which x is a mean number expressed as a percentage ranging from 70 to 100; y is a mean number equal to 100−x. The range for x expressly includes 75, 80, 85, 90 and 95. There may be mentioned, for example, the products marketed under the names Airvols 103, 350, 203, 540, 714 and 603 by the company Air Products.

C) homopolymers and copolymers of vinylpyrrolidone, in particular, those having an average molar mass ranging from 10,000 g/mol to 1,000,000 g/mol. This range expressly includes 15,000, 20,000, 75,000, 100,000, 500,000, and 750,000 g/mol. They may be chosen from: 1) polyvinylpyrrolidones having the following formula (XV):

(XV)

There may be mentioned, for example, the products marketed under the names Polyclar V15 (molar mass of about 8000 g/mol), V30 (molar mass of about 50,000 g/mol), V60 (molar mass of about 400,000 g/mol), V90 (molar mass of about 1,000,000 g/mol) and V120 (molar mass of about 2,500,000 g/mol) by the company ISP.

2) copolymers of vinylpyrrolidone such as: (a) copolymers of vinylpyrrolidone and of vinyl acetate, in particular, the copolymer containing 30% of vinyl acetate, marketed under the name PVP-VA 735 by the company ISP; (b) copolymers of vinylpyrrolidone and of vinylpyrrolidone derivatives with butene grafts, such as the copolymer containing 10% vinylpyrrolidone with butene grafts, marketed under the name Ganex (or Antaron) P904 by the company ISP; (c) copolymers of vinylpyrrolidone and of maleic anhydride; (d) copolymers of vinylpyrrolidone with polyvinyl alkyl ethers of the following formula (XVI):

(XVI)

in which R is chosen from the alkyl groups containing from 1 to 7 carbon atoms. This range expressly includes 2, 3, 4, 5, and 6 carbons. Preferably, R is a methyl group; (e) copolymers of vinylpyrrolidone and of N-vinyllactams such as N-butyrolactam and N-vinylcaprolactam; (f) copolymers of vinylpyrrolidone with the neutral acrylic derivatives of the following formula (XVII):

(XVII)

in which R is hydrogen or a methyl group, and X is chosen from the groups alkyl oxide of the type OR' where R' contains from 1 to 7 carbon atoms (which range expressly includes 2, 3, 4, 5, and 6 carbons); hydroxylated and/or aminated alkyl oxide of the $OR_1(OH)_n(NR_2R_3)_m$ type where n and m are numbers ranging from 0 to 10 (which range expressly includes 1, 2, 3, 4, 5, 6, 7, 8 and 9). $R_1$ is an alkyl group containing from 1 to 7 carbon atoms (which range expressly includes 1, 2, 3, 4, 5, 6, 7, 8 and 9); $R_2$ and $R_3$ are independently hydrogen or an alkyl group such that the sum of the carbon atoms of $R_2$ and $R_3$ ranges from 1 to 7 (which range expressly includes 2, 3, 4, 5, and 6); primary, secondary or tertiary amine of the $NR_2R_3$ type where $R_2$ and $R_3$ have the meaning indicated above.

D) homopolymers and copolymers of vinyl caprolactam which may be chosen from: 1) polyvinylcaprolactams which have the following formula (XVIII):

(XVIII)

2) copolymers of vinylcaprolactams obtained from vinylcaprolactam and from one or more of the following monomers: vinyl acetate; N-vinyllactam such as N-butyrolactam, N-vinylcaprolactam and N-vinylpyrrolidone; maleic anhydride; vinyl alkyl ethers of formula (XVI) indicated above; neutral acrylic derivatives of formula (XVII) indicated above.

As polymers and copolymers of this type, there may be mentioned, for example, the product marketed under the name Luviskol Plus by the company BASF and the product marketed under the name H2OLD EP-1 by the company ISP.

E) homopolymers and copolymers of polyvinyl methyl ether which may be chosen from: 1) polyvinyl methyl ethers of formula (XVI) indicated above; 2) copolymers obtained from vinyl methyl ether and from one or more of the following monomers:

vinyl alkyl ethers of formula (XVI) indicated above; vinyl acetate; N-vinyllactam such as N-butyrolactam, N-vinylcaprolactam and N-vinylpyrrolidone; maleic anhydride; neutral acrylic derivatives of formula (XVII) indicated above.

As polymers and copolymers of this type, there may be mentioned, for example, the products marketed under the names Gantrez (INCI name: PVM/MA copolymer), and particularly Gantrez AN-119 (molar mass of about 190,000 g/mol), AN-139 (molar mass of about 950,000 g/mol), AN-149 (molar mass—1,100,000 g/mol), AN-169 (molar mass of about 1,700,000 g/mol) and AN-179 (molar mass of about 2,000,000 g/mol) by the company ISP.

F) neutral acrylic homopolymers and copolymers, in particular, those having a molar mass ranging from 10,000 g/mol to 5,000,000 g/mol. This range expressly includes 20,000, 50,000, 100,000, 500,000, 1,000,000 and 2,500,000 g/mol. They may be chosen from:
1) neutral water-soluble acrylic polymers having the following formula (XIX):

in which $R_1$ is hydrogen or a methyl group, and X is chosen from (a) alkylamino groups or (b) hydroxylated and/or aminated alkyl oxide groups.

The polymers with (a) alkylamino groups are compounds of formula (XIX) where $X=NR_2R_3$ such that the corresponding acrylic polymer is water-soluble, $R_2$ and $R_3$ being independently hydrogen or an alkyl group such that the sum of the carbon atoms of $R_2$ and $R_3$ ranges from 1 to 7 (which range expressly includes 2, 3, 4, 5, and 6). As polymers of this type, there may be mentioned in particular polyacrylamides where $R_1$, $R_2$ and $R_3$ are hydrogen; polymethylacrylamides where $R_1$ is a methyl group and $R_2$ and $R_3$ are hydrogen; poly-N-methylacrylamides where $R_1$ and $R_2$ are hydrogen and $R_3$ is a methyl group; poly-N,N'-dimethylacrylamides where $R_1$ is hydrogen and $R_2$ and $R_3$ are a methyl group; poly-N-ethylacrylamides where $R_1$ and $R_2$ are hydrogen and $R_3$ is an ethyl group; poly-N-isopropylacrylamides where $R_1$ and $R_2$ are hydrogen and $R_3$ is an isopropyl group.

As a polymer of this type, there may be mentioned the polyacrylamide marketed under the name Superfloc N300 LMW by the company Cytec.

Polymers with hydroxylated and/or aminated alkyl oxide groups (b) are compounds of formula (XIX) in which $X=OR_2(OH)_n(NR_3R_4)_m$ where n and m are numbers ranging from 0 to 10 (which range expressly includes 1, 2, 3, 4, 5, 6, 7, 8, and 9), $R_2$ is an alkyl group containing from 1 to 7 carbon atoms (which range expressly includes 2, 3, 4, 5, and 6); $R_3$ and $R_4$ are independently hydrogen or an alkyl group such that the sum of the carbon atoms of $R_3$ and $R_4$ ranges from 1 to 7 (which range expressly includes 2, 3, 4, 5, and 6), these groups being such that the corresponding acrylic derivative is water-soluble.

As a polymer of this type, there may be mentioned the polyglyceryl methacrylate marketed under the name Lubrajel CG by the company Guardian.

2) copolymers of a water-soluble and neutral acrylic derivative of formula (XIX) as defined above and of one or more of the following neutral monomers: vinyl acetate; N-vinyllactam such as N-butyrolactam, N-vinylcaprolactam and N-vinylpyrrolidone; maleic anhydride; vinyl alkyl ethers of formula (XV) indicated above; neutral acrylic derivative of formula (XVII) indicated above.

G) $C_1$-$C_2$ alkyl celluloses and their neutral derivatives, in particular those having a molar mass ranging from 10,000 g/mol to 5,000,000 g/mol. This range expressly includes 20,000, 50,000, 100,000, 500,000, 1,000,000 and 2,500,000 g/mol. They may be chosen in particular from hydroxyethyl cellulose, such as the product marketed under the names Natrosols 250 LR and 250 HHR by the company Aqualon; ethylhydroxyethyl cellulose, such as the products marketed under the names Elfacos CD 481 and CD 411 by the company Akzo Nobel; methyl cellulose and methylhydroxyalkyl celluloses, such as the product marketed under the name Methocel A4C by the company Dow Chemical and the products marketed under the names 10 Benecel by the company Hercules.

H) $C_1$-$C_3$ alkyl guar or $C_1$-$C_3$ hydroxyalkyl guar, in particular, those having a molar mass ranging from 10,000 g/mol to 5,000,000 g/mol. This range expressly includes 20,000, 50,000, 100,000, 500,000, 1,000,000 and 2,500,000 g/mol. There may be mentioned hydroxypropyl guar, such as the product marketed under the name Jaguar HP-105 by the company Rhodia.

According to the invention, the water-soluble non-ionic polymers may represent a quantity of 0.01% to 20% by weight, preferably of 0.05% to 10% by weight and more particularly of 0.1% to 5% by weight, relative to the total weight of the composition.

Particle Size

The size of the particles of the meta-stable cosmetic composition in the form of an oil-in-water emulsion may be about 0.2 microns (200 nm) to about 50 microns (50,000 nm) or alternatively about 0.2 microns (200 nm) to about 10 microns (10000 nm).

The meta-stable cosmetic composition can be made utilizing any suitable mixing device, such as a rotor stator. However, in another embodiment, the meta-stable cosmetic composition may be formed using a high pressure homogenizer. Formation using the high pressure homogenizers permit control of the particle size.

Hydrophilic-Lipophilic Balance (HLB)

Hydrophile-lipophile balance is an empirical expression for the relationship of the hydrophilic ("water-loving") and hydrophobic ("water-hating") groups of a surfactant. The HLB system is particularly useful to prepare O/W and W/O emulsions. Water-in-oil emulsions (W/O) require low HLB surfactants, having an HLB value of equal to or less than 6. Oil-in-water emulsions (O/W) require high HLB surfactants having an HLB value equal to or greater than 9. The total HLB of surfactants can be calculated by taking the weight percent of each surfactant of the surfactant mixture and multiplying the weight percent by the HLB to obtain a contribution of each individual surfactant on the HLB. The individual contributions are then added together to get the total HLB of the surfactant mixture. HLBs for individual surfactants are usually provided in the literature or provided by the surfactant supplier. For example, if the surfactant mixture is a 50/30/20 blend of polysorbate 61, octyldodecyl xyloside and glyceryl stearate the total HLB of the 50/30/20 surfactant mixture is 7.11. The HLB of polysorbate 61 is 9.4, the HLB of octyldodecyl xyloside is 5.5, and the HLB of glyceryl stearate 3.8. The contribution of polysorbate 61 is 0.5×9.4=4.7. The contribution of octyldodecyl xyloside is 0.3×5.5=1.65. The contribution of glyceryl stearate is 0.2× 3.8=0.76. The total HLB is 4.7+1.65+0.76=7.11.

The meta-stable cosmetic composition has a ratio of the at least one non-ionic oil-in-water emulsifier to the at least one water-in-oil emulsifier is about 0.02 to about 2.0, or alternatively 0.2 to about 2.0, or alternatively about 0.3 to about 1.0, or alternatively about 0.3 to about 0.5.

A method for treating keratinous tissue includes applying to the keratinous tissue the meta-stable cosmetic composition of the present disclosure. The meta-stable cosmetic composition of the present disclosure is in any desirable cosmetic form, such as, but not limited to, sprays, liquid lotions, creams, mousses, and foams, can be applied to keratinous tissue to provide the desired cosmetic effect, such as, but not limited to, UV protection or hydration.

The compositions described above may be packaged, in a known manner, in a single-compartment bottle. The user must then shake the bottle before pouring or spraying the product onto skin. The product may also be packed in a bottle of the "pump dispenser" type. Provision may also be made for the two phases of the composition to be introduced into two independent compartments of the same bottle, a system being provided to mix them together at the time of dispensing. Such devices are described, for example, in documents EP-A-497 256 and FR-A-2 697 233. In another embodiment, the product may also be packed in an aerosol packaging system, such as a bag in can, bag on valve, piston in can or other similar packaging having two or more separate compartments or storage areas for the product and propellant.

Processes that can be used to make the inventive compositions include, but are not limited to, classical mixing, high pressure homogenization, Symex, hold-cold, or dilution.

The present invention will be better understood from the examples that follow, all of which are intended for illustrative purposes only and are not meant to unduly limit the scope of the invention in any way.

EXAMPLES

Having generally described this invention, a further understanding can be obtained by reference to certain specific examples which are provided herein for purposes of illustration only and are not intended to be limiting unless otherwise specified. The amounts shown are in % by weight, unless otherwise mentioned.

In making each of the examples in Table 1 and 2, the following procedure is used. Water phase ingredients are weighed and added to a main reactor and heated to about 90° C. Oil phase ingredients are weighed and added to a second reactor and heated to 90° C. ingredients are added to the main reactor containing water phase ingredients and homogenized for 30 minutes while the temperature is maintained at 90° C. The mixture is cooled to room temperature. Tables 1 and 2 show examples of a meta-stable cosmetic composition according to an embodiment of the present disclosure. Other processes that can be used to make the inventive compositions include, but are not limited to, high pressure homogenization, Symex, or hold-cold.

TABLE 1

| Chemical Name | HLB | Ex. 1 (% by wt.) | Comp. Ex. 1 (% by wt.) |
|---|---|---|---|
| TRIETHANOLAMINE | | 0.1 | 0.1 |
| EMOLLIENT | | 13.5 | 13.5 |
| WAX | | 1.5 | 1.5 |
| ACRYLATES/C10-30 ALKYL ACRYLATE CROSSPOLYMER | | 0.1 | 0.1 |
| PEG-30 DIPOLYHYDROXYSTEARATE | 5.5 | 1.9 | |
| PRESERVATIVE | | 1.1 | 1.1 |
| AESTHETIC MODIFIER | | 1.92 | 1.92 |
| WATER | | 69.63 | 69.98 |
| GLYCERIN | | 5 | 5 |
| PROPANEDIOL | | 2 | 2 |
| GLYCERYL STEARATE (and) PEG-100 STEARATE | 11 | | 1.9 |
| POLYSORBATE 61 | 9.4 | 0.1 | |
| PEG-40 STEARATE | 16.9 | | 2.5 |
| SODIUM STEAROYL GLUTAMATE | | 0.25 | |
| OCTYLDODECANOL (and) OCTYLDODECYL XYLOSIDE | 5.5 | 2.5 | |
| GLYCERYL STEARATE | 3.8 | 0.4 | 0.4 |
| Total | | 100 | 100 |
| Properties | | | |
| Weight Ratio of OIL-IN-WATER Emulsifier to WATER-IN-OIL Emulsifier | | 0.03 | 1.09 |
| Forms Meta-Stable Composition | | Yes | No |

Figure 1:
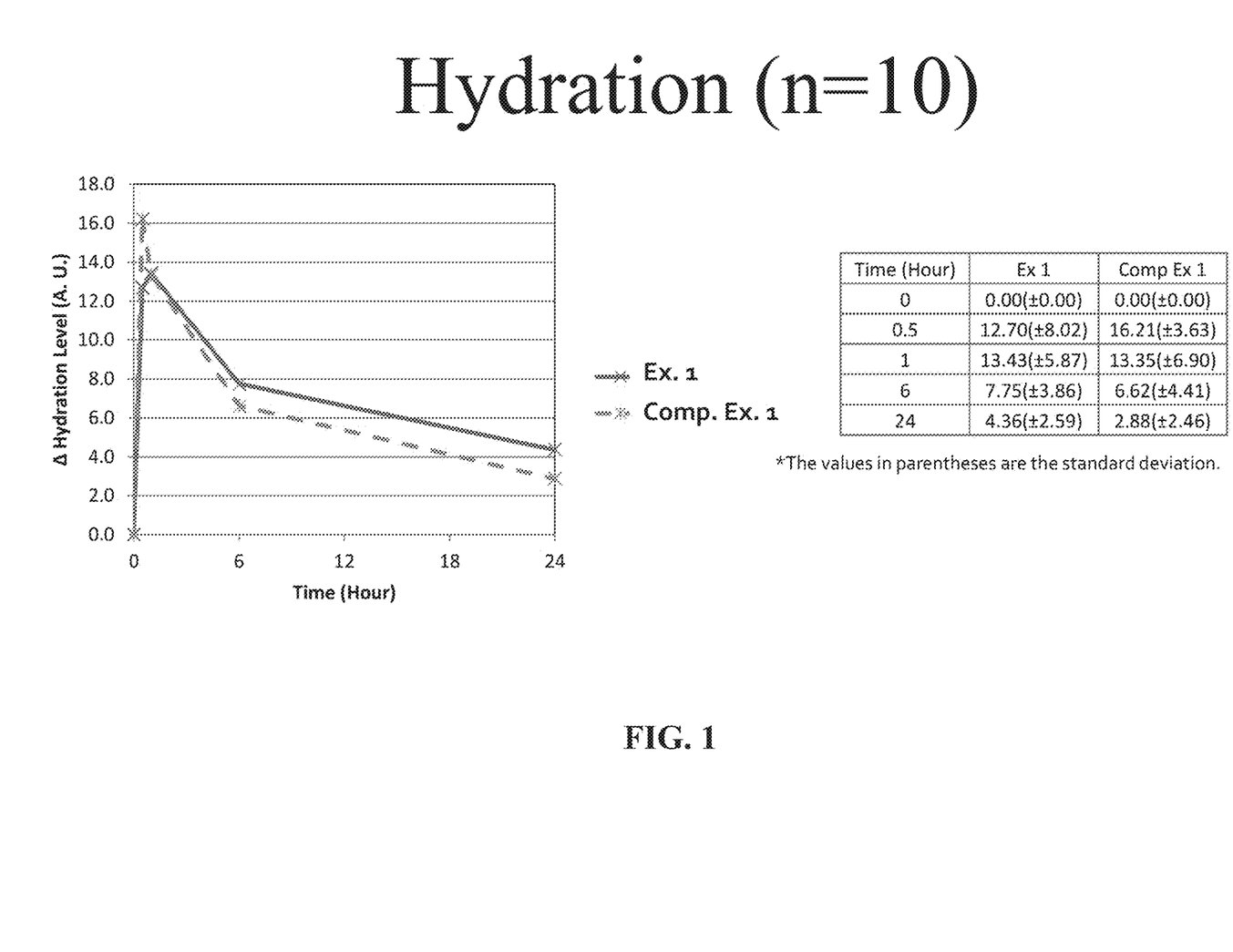
FIG. 1 shows a comparison of hydration of a Comparative Example versus an Inventive Example formulation according to the present disclosure.

FIG. 1 shows hydration of Inventive Example (Ex. 1) according to an embodiment of the invention shown in Table 1 versus the hydration of Comparative Example 1 (Comp. Ex. 1). Hydration was measured with a Corneometer® as a change in hydration level and was subtracted from the baseline and the untreated site. The Corneometer® used to measure the hydration index was Corneometer® CM825, available from Courage Khazaka, Cologne, Germany. The Corneometer® readings were taken were taken at a temperature of 20.5° C. and relative humidity of 46%.

Figure 2:
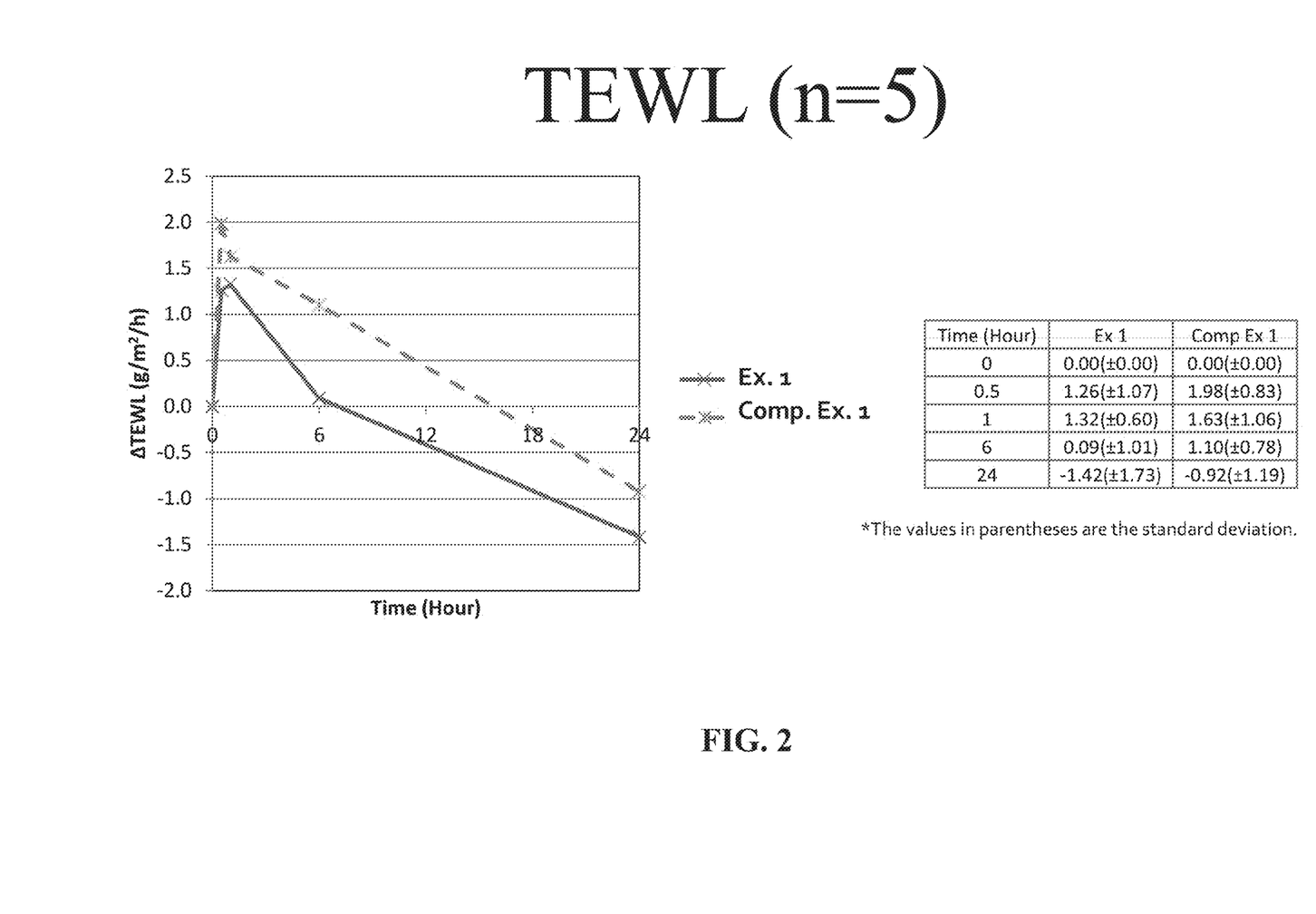
FIG. 2 shows a comparison of Transepidermal Water Loss (TEWL) of a Comparative Example versus an Inventive Example formulation according to the present disclosure.

FIG. 2 shows Transepidermal Water Loss (TEWL) of Ex. 1 according to an embodiment of the invention shown in Table 1 versus the hydration of Comp. Ex. 1. The transepidermal water loss (TEWL) was measured using Transepidermal water loss was measured on the volar forearms with Aquaflux™ AF200 (Biox Systems. Ltd., London, UK) on the same test sites and at the same time points of the subjects who were also in the hydration measurement described above.

TABLE 2 shows example of compositions according to the present disclosure including measured hydration levels.

TABLE 2

| Chemical Name | 7.5% glycerin Ex. 2 (% by wt.) | 15% glycerin Ex. 3 (% by wt.) | 20% oil, 20% glycerin Ex. 4 (% by wt.) | 7.5% glycerin, 20% shea butter Ex. 5 (% by wt.) | low viscosity spray 10% glycerin, 11% oil Ex. 6 (% by wt.) | 16% oil Ex. 7 (% by wt.) |
|---|---|---|---|---|---|---|
| TRIETHANOLAMINE | 0.4 | 0.4 | 0.4 | 0.4 | 0.17 | 0.17 |
| EMOLLIENT | 8.5 | 8.5 | 13.1 | 28 | 8.5 | 13.5 |
| WAX | 1.5 | 1.5 | 1.5 | 1.5 | 1.5 | 1.5 |
| STEARYL ALCOHOL | 0.18 | 0.18 | 0.18 | 0.18 | 0.18 | 0.2 |
| ALUMINUM STARCH OCTENYLSUCCINATE | 4 | 4 | 4 | 4 | 4 | 4 |
| ACRYLATES/C10-30 ALKYL ACRYLATE CROSSPOLYMER | 0.3 | 0.3 | 0.3 | 0.3 | 0.15 | 0.1 |
| AMMONIUM ACRYLOYL-DIMETHYLTAURATE/STEARETH-8 METHACRYLATE COPOLYMER | 0.55 | 0.55 | 0.1 | | | |
| PRESERVATIVE | 1.1 | 1.1 | 1.3 | 2.1 | 1.6 | 1.6 |
| AESTHETIC MODIFIER | 1.92 | 1.92 | 6.95 | 2.5 | 1.92 | 1.92 |
| WATER | 66.92 | 59.42 | 43.04 | 46.21 | 64.85 | 59.41 |
| GLYCERIN | 7.5 | 15 | 20 | 7.5 | 10 | 10 |
| PROPANEDIOL | 5 | 5 | 7 | 5 | 5 | 5 |
| POLYSORBATE 61 | 0.25 | 0.25 | 0.25 | 0.3 | 0.25 | 0.5 |
| SODIUM STEAROYL GLUTAMATE | 0.45 | 0.45 | 0.45 | 0.45 | 0.45 | 0.5 |
| OCTYLDODECANOL (and) OCTYLDODECYL XYLOSIDE | 1.07 | 1.07 | 1.07 | 1.2 | 1.07 | 1.2 |
| GLYCERYL STEARATE | 0.36 | 0.36 | 0.36 | 0.36 | 0.36 | 0.4 |
| Total | 100 | 100 | 100 | 100 | 100 | 100 |
| Properties | | | | | | |
| Change in hydration (1 hour) | 19.6 | 23.4 | 29.7 | 21 | 14.1 | 17.1 |
| Weight Ratio of OIL-IN-WATER Emulsifier to WATER-IN-OIL Emulsifier | 0.17 | 0.17 | 0.17 | 0.19 | 0.17 | 0.31 |
| Forms Meta-Stable Composition | Yes | Yes | Yes | Yes | Yes | Yes |

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A meta-stable cosmetic composition comprising:
   at least one water-in-oil emulsifier having a hydrophilic-lipophilic balance (HLB) of less than 6;
   at least one non-ionic oil-in-water emulsifier having an HLB of greater than 9;
   at least one ionic surfactant; and
   at least one care active ingredient;
   wherein the weight ratio of the at least one non-ionic oil-in-water emulsifier to the at least one water-in-oil emulsifier is from 0.3 to 0.5.

2. The meta-stable cosmetic composition of claim 1, wherein the combined concentration by weight of the at least one water-in-oil emulsifier, the at least one non-ionic oil-in-water emulsifier and the at least one ionic surfactant does not exceed about 6% by weight, based on the total weight of the composition.

3. The meta-stable cosmetic composition of claim 1, wherein the at least one water-in-oil emulsifier is present in an amount of from about 0.7% to about 5.0% by weight, based on the total weight of the composition.

4. The meta-stable cosmetic composition of claim 1, wherein the at least one non-ionic oil-in-water emulsifier is present in an amount of from about 0.1% to about 2.0% by weight, based on the total weight of the composition.

5. The meta-stable cosmetic composition of claim 1, wherein the at least one ionic surfactant is present in an amount of from about 0.1% to about 1.0% by weight, based on the total weight of the composition.

6. The meta-stable cosmetic composition of claim 1, wherein the at least one water-in-oil emulsifier is selected from the group consisting of sucrose distearate, polyglyceryl-4 isostearate (and) cetyl PEG/PPG 10/1 dimethicone (and) hexyl laurate, sorbitan stearate, octyldodecyl xyloside, glyceryl stearate, and combinations thereof.

7. The meta-stable cosmetic composition of claim 1, wherein the at least one non-ionic oil-in-water emulsifier is selected from the group consisting of PEG-40 stearate, polysorbate-61, and combinations thereof.

8. The meta-stable cosmetic composition of claim 1, wherein the at least one ionic surfactant is selected from the group consisting of sodium stearoyl glutamate, potassium cetyl phosphate, disodium stearoyl glutamate, and combinations thereof.

9. The meta-stable cosmetic composition of claim 1, wherein the skin care active ingredient is selected from the group consisting of dermatological active ingredients, emollients, humectants, hydrating active ingredients, and combinations thereof.

10. The meta-stable cosmetic composition of claim 9, wherein the at least one skin care active ingredient is present in an amount of from about 1% to about 40% by weight, based on the total weight of the composition.

11. The meta-stable cosmetic composition of claim 9, wherein the active ingredient includes an emollient.

12. The meta-stable cosmetic composition of claim 1, wherein the composition is an oil-in-water emulsion that inverts to a water-in-oil emulsion upon rubbing.

13. The meta-stable cosmetic composition of claim 1, wherein the composition includes an oil phase, the oil phase containing surfactants, wherein the surfactants comprise less than 40% by weight of the oil phase.

14. The meta-stable cosmetic composition of claim 1, wherein the composition includes an oil phase, the oil phase containing surfactants, wherein the surfactants comprise less than 35% by weight of the oil phase.

15. The meta-stable cosmetic composition of claim 1, wherein the composition includes an oil phase, the oil phase containing surfactants, wherein the surfactants comprise less than 31% by weight of the oil phase.

16. A product formed from a meta-stable cosmetic composition comprising:
   at least one water-in-oil emulsifier having a hydrophilic-lipophilic balance (HLB) of less than 6;
   at least one non-ionic oil-in-water emulsifier having an HLB of greater than 9;
   at least one ionic surfactant; and
   at least one skin care active ingredient;
   wherein the ratio of the at least one non-ionic oil-in-water emulsifier to the at least one water-in-oil emulsifier is from 0.3 to 0.5.

17. A meta-stable cosmetic composition comprising:
   at least one water-in-oil emulsifier having a hydrophilic-lipophilic balance (HLB) of less than 6;
   at least one non-ionic oil-in-water emulsifier having an HLB of greater than 9;
   at least one ionic surfactant; and
   at least one skin care active ingredient;
   wherein the weight ratio of the at least one non-ionic oil-in-water emulsifier to the at least one water-in-oil emulsifier is one of about 0.02, about 0.2 and about 0.3.

18. A meta-stable cosmetic composition of claim 17, wherein the at least one water-in-oil emulsifier is present in an amount of from about 0.7% to about 5.0% by weight, based on the total weight of the composition, and wherein the at least one non-ionic oil-in-water emulsifier is present in an amount of from about 0.1% to about 2.0% by weight, based on the total weight of the composition.

19. A product formed from a meta-stable cosmetic composition comprising:
   at least one water-in-oil emulsifier having a hydrophilic-lipophilic balance (HLB) of less than 6;
   at least one non-ionic oil-in-water emulsifier having an HLB of greater than 9;
   at least one ionic surfactant; and
   at least one skin care active ingredient;
   wherein the ratio of the at least one non-ionic oil-in-water emulsifier to the at least one water-in-oil emulsifier is one of about 0.02, about 0.2, and about 0.3.

20. A product formed from a meta-stable cosmetic composition of claim 19, wherein the at least one water-in-oil emulsifier is present in an amount of from about 0.7% to about 5.0% by weight, based on the total weight of the composition, and wherein the at least one non-ionic oil-in-water emulsifier is present in an amount of from about 0.1% to about 2.0% by weight, based on the total weight of the composition.

21. A cosmetic composition comprising:
   at least one water-in-oil emulsifier having a hydrophilic-lipophilic balance (HLB) of less than 6 present in an amount of from about 0.7% to about 5.0% by weight, based on the total weight of the composition;
   at least one non-ionic oil-in-water emulsifier having an HLB of greater than 9 present in an amount of from about 0.1% to about 2.0% by weight, based on the total weight of the composition;
   at least one ionic surfactant present in an amount of from about 0.1% to about 1.0% by weight, based on the total weight of the composition; and
   at least one skin care active ingredient;
   wherein the weight ratio of the at least one non-ionic oil-in-water emulsifier to the at least one water-in-oil emulsifier is from 0.3 to 0.5, and wherein the combined concentration by weight of the at least one water-in-oil emulsifier, the at least one non-ionic oil-in-water emulsifier and the at least one ionic surfactant does not exceed about 6% by weight, based on the total weight of the composition, and wherein the composition is an oil-in-water emulsion that inverts to a water-in-oil emulsion upon rubbing, and exhibits storage stability of at least one month at about 45 degrees C.

* * * * *